(12) United States Patent
Chen et al.

(10) Patent No.: US 6,261,538 B1
(45) Date of Patent: Jul. 17, 2001

(54) SERIES OF WATER-INSOLUBLE POLYMERIC QUATERNARY PHOSPHONIUM SALT USED FOR BACTERICIDES

(75) Inventors: Yongjun Chen; Xieqing Wang; Bengao Li, all of Beijing (CN)

(73) Assignees: China Petrochemical Corporation; Research Institute of Petroleum Processing, SINOPEC, both of Beijing (CN)

(*) Notice: Subject to any disclaimer, the term of this patent is extended or adjusted under 35 U.S.C. 154(b) by 0 days.

(21) Appl. No.: 09/179,965

(22) Filed: Oct. 28, 1998

(30) Foreign Application Priority Data

Oct. 28, 1997 (CN) ............................................. 97 1 19933

(51) Int. Cl.$^7$ .............................. A61L 9/04; C08F 30/02
(52) U.S. Cl. ..................... 424/45; 424/78.31; 424/78.35; 424/78.32; 424/405; 424/409; 526/278; 525/331.3; 525/331.4
(58) Field of Search .............................. 424/451, 78.35, 424/78.31, 78.32, 405, 409; 526/278; 525/331.3, 331.4

(56) References Cited

U.S. PATENT DOCUMENTS 4,826,924 * 5/1989 Kourai et al. .................... 525/331.3
5,366,727 * 11/1994 Kanazawa et al. .............. 424/78.35

FOREIGN PATENT DOCUMENTS 971167265 8/1997 (CN).
5310820 11/1993 (JP).

OTHER PUBLICATIONS

J. Polymer Sci Part A: Polymer Chemistry, vol. 31, No. 2 pp. 335–343, Feb. 1993.*
J. Applied Polymer Science vol. 53, No. 9 pp. 1245–1249, Feb. 1993.*
Kanazawa et al. Polymeric Phosphonium Salts as a Novel Class of Cationic Biocides, VII. Synthesis and Antibacterial Polymeric Phosphonium Salts and Their Model Compounds Containing Long Alkyl Chains, J. Applied Polymer Science, vol. 53, p.p. 1237–1244 (1994).

* cited by examiner

Primary Examiner—Bennett Celsa
(74) Attorney, Agent, or Firm—Birch, Stewart, Kolasch & Birch, LLP (57) ABSTRACT

Disclosed is a series of the water-insoluble polymeric quaternary phosphonium salt-type bactericides, which consists of as active bactericidal components an amino quaternary phosphonium salt, a quaternary ammonium group-containing quaternary phosphonium salt, an amino quaternary phosphonium salt-quaternay ammonium salt, or a quaternary ammonium salt-containing quaternary phosphonium salt and quaternary ammonium salt carried on a resin carrier which can be chloromethylated. Said bactericide series has rapid and highly effective bactericidal activity, and can be used repeatedly, and used widely for sterilizing and disinfecting various fluid media such as different industrial and domestic water and the like.

5 Claims, 5 Drawing Sheets

SERIES OF WATER-INSOLUBLE POLYMERIC QUATERNARY PHOSPHONIUM SALT USED FOR BACTERICIDES

BACKGROUND OF THE INVENTION

1. Field of the Invention

The invention relates to a disinfectant. More particularly, it relates to a series of water-insoluble polymeric quaternary phosphonium salts used for bactericides in which a resin is used as a carrier.

2. Discussion of the Prior Art

Development of water-insoluble polymeric bactericides has been started on in order to overcome the drawbacks such as, for example, high poison, easily foaming etc., of water-soluble bactericides, in U.S. Pat. No. 4,349,646, a water-insoluble polymeric quaternary ammonium salt type of bactericide having different structures is prepared by reacting a chloromethyl-containing resin (such as a chloromthylated and crosslinked or uncrosslinked polystyrene resin or a polychloromethyl-acrylate resin) with tertiary amine, di-tertiary-group diamine. In U.S. Pat. No. 4,826,924, a nitrogen-containing polymer type of bactericide is prepared by reacting a chloromethyl-containing polystyrene or polystyrene-divinylbenzene resin with a bipyridinonium having a long chain alkyl or a tert-amino quaternary ammonium salt. In the application of CN 97,116726.5, the inventors of the present invention describes that an amphoteric polymer type of batericide has been prepared by carrying an amino acid-type surfactant on a chloromethylated polystyrene-divinyl benzene resin.

The above-listed bactericides are all the water-insoluble nitrogen-containing bactericide. In recent years, along with the deepening of the study of a water-soluble quaternary ammonium salt type bactericide and a water-soluble quaternary phosphonium salt type bactericide, it has been found that the bactericidal activity of the quaternary phosphonium type bactericides is higher than that of the quaternary ammonium salt type bactericides with similar structures. Thus, it can be assumed that if a water-insoluble polymeric quaternary phosphonium type bactericide is prepared by carrying a quaternary phosphonium salt having batericidal activity on a resin, much higher bacteridical effect will be expectantly obtained. However, it is difficult to carry a quaternary phosphonium salt on a resin technically. At present there are some reports in this area in the world. Akihiko describes a method for synthesizing a polymeric quaternary phosphonium salt in "Polymeric Phosphonium Salts as a Novel Class of Cationic Biocides. X." (cf. Journal of Applied Polymer Science, Vol. 54, 1305–1310, 1994), that is to say, by firstly carrying out the quaterisation of a long chain of tertiary phosphine with chloromethyl styrene, and then polymerizing the resulting product, i. e. carrying the active groups on the resin prior to the polymerization. Although the polymeric quaternary phosphonium salt obtained by this method has highly effective and rapid bactericidal effect, there are some defects as below: (1) the starting materials are not easy to obtain, the chloromethyl styrene and tertiary phosphine used by the authors are not available as commercial products, and the conditions of reaction when prepared in laboratory are very stricted: (2) it is very difficult to increase the degree of polymerization by using the method of carrying active groups prior to the polymerization, thus the product obtained still has a certain content of solubility in water.

JP 5310820 reports that an insoluble polymeric quaternary phosphonium salt is prepared by carrying a quaternary phosphonium salt-type bactericide on a polymer carrier through the electrostatic effect between the anionic ion, such as $-SO_3-$, of the polymer and the cationic ion of the quaternary phosphonium salt. But, the most important defect of the polymeric quaternary phosphonium salt obtained by this method is that the combination between the quaternary phosphonium salt, which is carried on the resin only by the electrostatic effect between anionic ion and cationic ion, and such a combination is not strong enough, so that the bactericide can be easily stripped from the resin into aqueous phase while treated by using water, thereby resulting in environmental pollution.

An object of the present invention is to provide a novel water-insoluble polymeric quaternary phosphonium salt type bactericide series in order to overcome the drawbacks of the prior art. The bactericide series of the present invention not only has a rapid and highly effective bactericidal activity, but also can be used repeatedly.

SUMMARY OF THE INVENTION

The series of the water-insolube polymeric quaternary phosphonium salt type bactericides according to the present invention comprises four classes of the bactericides. They are composed of, as active bactericidal components, an amino quaternary phosphonium salt, a quaternary ammonium group-containing quaternary phosphonium salt, an amino quaternary phosphonium salt-quaternary ammonium salt, and a quaternary ammonium group-containing quaternary phosphonium salt-quaternary ammonium salt respectively carried on a resin which can be the chloromethylated as a carrier.

The first class of the bactericides consists of two parts including a resin carrier and an amino quaternary phosphonium salt. Its structural formula is as below:

(I)

where [P] is the resin which can be chloromethylated, R is $C_4 \sim C_{24}$ alkyl; n is an integer of 2~10; $R_1$, $R_2$ and $R_3$ are $C_1 \sim C_8$ alkyl; k is the carried amount of the functional group amino quaternary phosphonium salt per gram of the bactericide; $X^{-a}$ is selected from $Cl^-$, $Br^-$, $I^-$, $NO_3^-$, $SO_4^{2-}$, $CO_3^{2-}$ or $OH^-$; a is the valence of X.

The second class of the bactericides consists of two parts including a resin carrier and a quaternary ammonium group-containing quaternary phosphonium salt Its structural formula is as below:

(II)

where [P] is the resin which can be chloromethylated; R is $C_4 \sim C_{24}$ alkyl; R' is $C_1 \sim C_{18}$ alkyl; m is the carried amount of the quaternary ammonium group per gram of the bactericide; n is an integer of 2~10; $R_1$, $R_2$ and $R_3$ are $C_1 \sim C_8$ alkyl, k is the carried amount of the functional group quaternary phosphonium salt per gram of the bactericide, $X^{-a}$ is selected from $Cl^-$, $Br^-$, $I^-$, $NO_3^-$, $SO_4^{2-}$, $CO_3^{2-}$ or $OH^-$, a is the valence of X.

The third class of the bactericides consists of three parts including a resin carrier, an amino quaternary phosphonium salt and a quaternary ammonium salt. Its structural formula is as below:

(III)

where [P] is the resin which can be chloromethylated; R is $C_4$~$C_{24}$ alkyl; n is an integer of 2 ~10; $R_1$, $R_2$ and $R_3$ are $C_1$~$C_8$ alkyl; k is the carried amount of the functional group amino quaternary phosphonium salt per gram of the bactericide; $X^{-a}$ is selected from $Cl^-$, $Br^-$, $I^-$, $NO_3^-$, $SO_4^{2-}$, $CO_3^{2-}$ or $OH^-$; a is the valence of X; Q is an aliphatic tertiary amine; and f is the carried amount of the quaternary ammonium salt per gram of the bactericide.

The fourth class of the bactericides consists of three parts including a resin carrier, a quaternary ammonium group-containing quaternary phosphonium salt and a quaternary ammonium salt. Its structural formula is as below:

(IV)

where [P] is the resin which can be chloromethylated; R is $C_4$~$C_{24}$ alkyl; R' is $C_1$~$C_{18}$ alkyl; m is the carried amount of the quaternary ammonium group per gram of the bactericide; n is an integer of 2~10; $R_1$,$R_2$ and $R_3$ are $C_1$~$C_8$ alkyl; k is the carried amount of the functional group quaternary phosphonium salt per gram of the bactericide; $X^{-a}$ is selected from $Cl^-$, $Br^-$, $I^-$, $NO_3^-$, $SO_4^{2-}$, $CO_3^{2-}$ or $OH^-$; a is the valence of X. Q is an aliphatic tertiary amine; f is the carried amount of the quaternary ammonium salt per gram of the bactericide.

DETAILED DESCRIPTION OF THE INVENTION

The water-insoluble polymeric quaternary phosphonium salt type bactericide series according to the present invention comprises four classes of the bactericides. They consist of, as active bactericidal components, an amino quaternary phosphonium salt, a quaternary ammonium group-containing quaternary phosphonium salt, an amino quaternary phosphonium salt-quaternary ammonium salt, and a quaternary ammonium group-containing quaternary phosphonium salt-quaternary ammonium salt, respectively carried on the resin carrier which can be chloromethylated.

The first class of the bactericides according to the present invention consists of two parts including a resin carrier and an amino quaternary phosphonium salt. Its structural formula is as below:

(I)

where [P] is the resin which can be chloromethylated, R is $C_4$~$C_{24}$ alkyl, n is an integer of 2~10, $R_1$, $R_2$ and $R_3$ are $C_1$~$C_8$ alkyl, k is the carried amount of the functional group amino quaternary phosphonium salt per gram of the bactericide, $X^{-a}$ is selected from $Cl^-$, $Br^-$, $I^-$, $NO_3^-$, $SO_4^{2-}$, $CO_3^{2-}$ or $OH^-$, and a is the valence of X.

The structural formula of said resin carrier part is [P]—$CH_2$—. The resin [P] is preferably a polystyrene resin or a gel or large pore type resin obtained by copolymerizing styrene and divinylbenzene. The crosslinked degree of the gel type resin may be 1~15%, preferably 1~4%; the crosslinked degree of the large pore type resin may be 1~20%, preferably 1~10%.

The structural formula of the amino quaternary phosphonium salt part is:

wherein R is $C_4$~$C_{24}$ alkyl, preferably $C_6$~$C_{20}$ alkyl, most preferably $C_6$~$C_{16}$ linear or branch chain alkyl; n is an integer of 2~10, preferably 3~8, most preferably 3~6; $R_1$, $R_2$ and $R_3$ are $C_1$~$C_8$ alkyl, preferably $C_1$~$C_6$ alkyl, most preferably $C_1$~$C_4$ alkyl; $R_1$, $R_2$ and $R_3$ may be same or different; k is the carried amount of the functional group amino quaternary phosphonium salt per gram of the bactericide, which may be 0.1~1 mmol/g bactericide; generally 0.1~0.4 mmol/g bactericide is suitable; of course, the greater k value (i. e., the carried amount) is, the more advantageous it is to increasing the bactericidal activity.

In the structure of this class of bactericide, there is still a part of chlorine bound with the resin. Substituting this part of chlorine with an active group and introducing a hydrophilic quaternary ammonium group will result in further increasing of the bactericidal activity.

Said first class of bactericide according to the invention is prepared by the process as follows:

(1) preparation of haloalkyl trialkyl phosphoniums:

Alkyl dihalide and trialkyl phosphine are mixed, heated to a temperature of 20~100° C., reacted for 10~60 hrs, preferably 24~60 hrs while stirring, then cooled to room temperature, and a precipitant such as diethyl ether is added to separate solid, then filtered, and washed with the precipitant for 2~3 times, and dried at the temperature below 100° C.

Said alkyl dihalide has the following structure: $X_1(CH_2)_nX_2$, wherein $X_1$ and $X_2$ may be selected from Cl, Br or I; $X_1$ and $X_2$ may be same or different. If different, the following mixture is formed, It is not necessary to separate the two products, because both produets will be converted into the desired product in the next reaction with an amine. n is an integer of 2~10, preferably 3~8, most preferably 3~6. When n is 2~4, the reaction temperature will be room temperature or slightly lower, when n is 5~10, the reaction will be carried out at a relatively high temperature, e.g. 50~100° C. The reaction should be conducted under nitrogen in order to avoid oxidation of trialkyl phosphine at elevated temperature.

Said trialkyl phosphine has the following structure:

wherein $R_1$, $R_2$ and $R_3$ are same or different $C_1$~$C_8$ alkyl, preferably $C_1$~$C_6$ alkyl.

The amount of the alkyl dihalide will be appropriately more excessive than that of trialkyl phosphine in order to avoid the formation of bis-quaternary phosphonium salt from a reaction between two halogen atoms of the alkyl dihalide and trialkyl phosphine, for example, the moles of trialkyl phosphine may be 0.4~0.9 times of that of the alkyl dihalide, preferably 0.5~0.8 times. Additionally, the trialkyl phosphine is preferably added dropwise into the alkyl dihalide when the reaction is conducted.

The reaction equation of the above-said process is as follows:

The resulting two products are all the haloalkyl trialkyl phosphoniums.

(2) preparation of the amino quaternary phosphoniums:

The solution of primary amine, base or basic salt and haloalkyl trialkyl phosphonium in an organic solvent is mixed, in which the mole ratio of haloalkyl trialkyl phosphonium, base or basic salt and primary amine is 1:1:1~5, heated until reflux occurs, reacted for 1~6 hrs, preferably 2~4 hrs, then the inorganic salt and solvent are removed, and a precipitant such as diethyl ether is added in the residue to obtain more solid, the resulting mixture is filtered, washed with the precipitant for 2–3 times, then dried at the temperature below 100° C. If amine is too excessive, the resulting solid will be recrystallized and purified with a mixed solvent of dichloromethane or chloroform or dioxane and diethyl ether, then the solid is dried again.

The structural formula of said primary amine is $RNH_2$, wherein R is $C_4$~$C_{24}$ alkyl, preferably $C_4$~$C_{20}$ alkyl, more preferably $C_6$~$C_{16}$ linear or branch chain alkyl. The amount of primary amine used should be equivalent or appropriately excessive relatively to the amount of haloalkyl trialkyl phosphonium in order to prevent the formation of tertiary amine, for example, the molar ratio of the two may be 1~5:1, preferably 1~3:1.

The act of said base and basic salt is to neutralize the hydrochloric acid formed during reaction. They may be selected from an inorganic base such as sodium hydroxide, aqueous ammonia and potassium hydroxide etc., or a basic inorganic salt such as sodium carbonate, potassium carbonate and sodium bicarbonate etc.,. The molar amount of base or basic salt used should be eqaul to that of haloalkyl trialkyl phosphonium in order to neutralize completely the hydrochloric acid formed.

The haloalkyl trialkyl phosphonium is preferably added dropwise when the reaction is conducted, The haloalkyl trialkyl phosphonium is firstly dissolved in an organic solvent to prepare a solution with a concentration of 0.25~1 g/ml, when added dropwise. The organic solvent for dissolving the haloalkyl trialkyl phosphonium can be selected according to the knowledge and prior arts well known to those skilled in the art, for example, $C_2$~$C_4$ alcohols, dioxane, nitrogen, nitrogen-dimethyl amide (DMF) and the like, and also a mixture of several solvents of them may be selected for use.

The reaction equation of the above-said reaction process is:

(3) preparation of polymeric amino quaternary phosphonium salts:

The chloromethylated resin, an organic solvent and the above amino quaternary phosphonium salt are mixed, reacted at reflux temperature for 10~80 hrs, preferably for 24~72 hrs, extracted with a solvent for 1~2 hrs to remove the unreacted amino quaternary phosphonium salt, then washed with hot ethanol at 30–75° C. or hot water for 2~3 times, then dried at a temperature below 100° C.

Said chloromethylated resin is preferably a chloromethylated polystyrene resin or a gel or large pore type resin obtained by copolymerizing styrene and divinylbenzene. The crosslinked degree of the gel type resin may be 1~10%, preferably 1~4%; the crosslinked degree of the large pore type resin may be 1~20%, preferably 1~10%. The chloromethyl group on the resin can be replaced by other groups having allyl structure such as, for example, bromonethyl, iodomethyl etc. The chlorine content of the resin can be 5~30%, preferably 10~25%.

Said organic solvent can not only make the resin swell, but also dissolve the amino quaternary phosphonium salt, for example, it may be $C_1$–$C_4$ alcohols, dioxane, tetrahydofuran etc., and also may be a mixture of several solvents of them. The amount of the organic solvent added is about 5~40 ml, preferably 10~20ml, per gram of the resin.

The amount of said amino quaternary phosphonium salt used may be determined on the basis of the molar amount of the cholorine contained in the resin, for example, the former may be 0.1~1 times of the latter, preferably 0.2~0.8 times. If the molar amount of the former used is greater than that of chlorine, it will result in extravagance, and, if the amount used is too little, the carried amount will be too little, and thus the bactericidal effect will be decreased.

The reaction equations of the above-said reaction are as follows:

After the reaction is completed, the $X^-$ of the product can further be ion-exchanged with other ions existing in the solution, therefore, the $X^-$ may be $Cl^-$, $Br^-$, $I^-$, $SO_4^{2-}$, $NO_3^-$, $CO_3^{2-}$, $OH^-$, etc. Furthermore, since the chlorine in the resin can not be replaced completely by the amino quaternary phosphonium salt, thus the carried amount of the amino quaternary phosphonium salt will be only in a certain range, which may be 0.1~1 mmol/g bactericide, generally 0.1~0.4 mmol/g bactericide is suitable.

The structural formula of the final bactericide product may be completely expressed by the following:

wherein k is the carried amount of the amino quaternary phosphonium salt per gram of the bactericide, a is the valence of X.

The second class of the bactericides according to the present invention consists of two parts including the resin carrier and the quaternary ammonium group-containing quaternary phosphonium salt. Its structural formula is as follows:

(II)

where [P] is the resin which can be chloromethylated, R is $C_4$~$C_{24}$ alkyl, R' is $C_1$~$C_{18}$ alkyl, m is the carried amount of the quaternary ammonium group per gram of the bactericide, n is an integer of 2~10, $R_1$, $R_2$ and $R_3$ are $C_1$~$C_8$ alkyl, k is the carried amount of the functional group amino quaternary phosphonium salt per gram of the bactericide, $X^{-a}$ is selected from $Cl^-$, $Br^-$, $I^-$, $NO_3^-$, $SO_4^{2-}$, $CO_3^{2-}$ or $OH^-$, and a is the valence of X.

The structural formula of said resin carrier part is [P]—$CH_2$—. The resin [P] is preferably a polystyrene resin or a gel or large pore type resin obtained by copolymerizing styrene and divinylbenzene. The crosslinked degree of the gel type resin may be 1~10%, preferably 1~4%; and the crosslinked degree of the large pore type resin may be 1–20%, preferably 1~10%.

The strucural formula of the part of said amino quaternary ammonium group-containing quaternary phosphonium salt is:

wherein R is $C_4$~$C_{24}$ alkyl, preferably $C_6$~$C_{20}$ alkyl, most preferably $C_6$~$C_{16}$ linear or branch chain alkyl; R' is $C_1$~$C_{18}$ alkyl, preferably $C_1$~$C_{12}$ linear or branch chain alkyl; m is the carried amount of the quaternary ammonium group per gram of the bactericide, which may be 0.1~0.8 mmol/g bactericide, generally 0.1~0.4 mmol/g bactericide is suitable; n is an integer of 2~10, preferably 3~8, most preferably 3~6; $R_1$, $R_2$ and $R_3$ are $C_1$~$C_8$ alkyl, preferably $C_1$~$C_6$ alkyl, most preferably $C_1$–$C_4$ alkyl, $R_1$, $R_2$ and $R_3$ may be same or different; k is the carried amount of the functional group quaternary phosphonium salt per gram of the bactericide, which may be 0.1~1 mmol/g bactericide, generally 0.1~0.4 mmol/g bactericide. The greater k and m values are, the more advantageous it is to increasing the bactericidal activity. However, the m value can not be greater than the k value.

In the structure of this class of bactericide, there is still a part of chlorine bound with the resin. Substituting this part of chlorine with an active group will result in further increase of the bactericidal activity.

Said second class of bactericide according to the invention may be prepared on the basis of the first class of bactericides, the particular method is as follows:

Alkyl halide, an organic solvent and the first class of bactericide are mixed, reacted at a temperature of 20~100° C., preferably 40~80° C., for 10~60 hrs, preferably 30~50 hrs, then filtered, and washed with a solvent for 1~2 times, and dried at a temperature below 100° C.

The structural formula of said alkyl halide is R'Y, where R' is $C_1$~$C_{18}$ alkyl, preferably $C_1$~$C_{12}$ linear or branch chain alkyl; wherein Y is halogen, which may be chlorine, bromine or iodine. The amount of the alkyl halide used is 0.1~3 mmol/g bactericide, preferably 0.1~1 mmol/g bactericide based on weight of the first class of bactericide.

Said organic solvent can make the resin swell, for example, it may either be $C_1$–$C_4$ alcohols, dioxane, tetrahydrofuran, etc., or a mixture of several solvents of them. The amount of the organic solvent used is 5~20 ml/g bactericide, preferably 10~20 ml/g bactericide based on the weight of the first class of bactericide.

Said solvent used for washing may be either said organic solvent or diethyl ether and its mixture with an organic solvent. The amount of solvent used when washing should be 2~20 times of the product volume, preferably 5~10 times.

The reaction equation of the process said above is:

-continued

The amount of the quaternary ammonium group formed by the quaterisation of alkyl halide R'Y in the desired product can be determined through the increased weight of the first class of bactericide as a starting material.

The third class of the bactericides according to the present invention consists of three parts including a resin carrier, an amino quaternary phosphonium salt and a quaternary ammonium salt. Its structural formula is as follows:

(III)

where [P] is the resin which can be chloromethylated, R is $C_4$~$C_{24}$ alkyl; n is an integer of 2~10; $R_1$, $R_2$ and $R_3$ are $C_1$~$C_8$ alkyl; k is the carried amount of the functional group amino quaternary phosphonium salt per gram of the bactericide; $X^{-a}$ is selected from $Cl^-$, $Br^-$, $I^-$, $NO_3^-$, $SO_4^{2-}$, $CO_3^{2-}$ or $OH^-$; a is the valence of X; Q is an aliphatic tertiary amine; f is the carried amount of quaternary ammonium salt per gram of the bactericide.

The structural formula of said resin carrier part is:

The resin [P] is preferably a polystyrene resin or a gel or large pore type of resin prepared by copolymerizing styrene and divinylbenzene. The crosslinked degree of the gel type resin may be 1~15%, preferably 1~4%; the crosslinked degree of the large pore type resin may be 1~20%, preferably 1~10%.

The structural formula of said amino quaternary phosphonium salt part is:

wherein R is $C_4$~$C_{24}$ alkyl, preferably $C_6$~$C_{20}$ alkyl, most preferably $C_6$~$C_{16}$ linear or branch chain alkyl; n is an integer of 2~10, preferably 3~8, most preferably 3~6; $R_1$, $R_2$ and $R_3$ are $C_1$~$C_8$ alkyl, preferably $C_1$~$C_6$ alkyl, most preferably $C_1$~$C_4$ alkyl, $R_1$, $R_2$ and $R_3$ may be same or different; k is the carried amount of the functional group amino quaternary phosphonium salt per gram of the bactericide, which may be 0.1~1 mmol/g bactericide, generally 0.1~0.4 mmol/g bactericide is suitable. Of course, the higher k value is, the more advantageous it is to increasing the bactericidal activity.

The structural formula of said quaternary ammonium salt part is -$[Q^+]_f \cdot X^{-a}_{f/a}$, wherein Q is an aliphatic tertiary amine, which may be one containing one N atom, and also several N atoms. For example, the tertiary amine containing one N atom may be $C_1$~$C_{18}$ trialkyl tertiary amine, preferably $C_1$~$C_{12}$ trialkyl teriary amine, more preferably at least one alkyl is $C_1$~$C_6$ alkyl; the tertiary amine containing several N atoms may be one having the formula: $R_aR_bN(CH_2)_pNR_cR_d$, wherein $R_a$, $R_b$, $R_c$, and $R_d$ may be $C_1$~$C_{18}$ alkyl, preferably $C_1$~$C_{12}$ alkyl, more preferably at least one alkyl of them is $C_1$~$C_6$ alkyl. p is an integer of 1~10, preferably 1~8, more preferably 2~5. Taking into account the steric effect, the chain length of $R_a$, $R_b$, $R_c$ and $R_d$ should be matched with that of methylenes. For the longer chain of methylenes, the chain length of $R_a$, $R_b$, $R_c$ and $R_d$ can not be too long, at least the alkyl linked to one of the nitrogen atoms therein should be shorter; in contrast, for the shorter chain of methylenes, the chain length of the alkyl may be increased correspondingly. f is the carried amount of the quaternary ammonium salt per gram of bactericide, it may be 0.1~5 mmol/g bactericide, generally 0.4~3.5 mmol/g bactericide is suitable.

Said third class of bactericide according to the invention may also be prepared on the basis of the first class of bactericide, the particular method is as follows:

Tertiary amine, an organic solvent and the first class of bactericide are mixed, reacted at the reflux temperature for 10~60 hrs, preferably 20~50 hrs, then the reaction solution is filtered, extracted under reflux to remove free tertiary amine, then filtered, washed and dried at a temperature below 100° C.

Said tertiary amine can be a tertiary amine containing one N atom, and can also be a tertiary amine containing several N atoms. For example, the tertiary amine having one N atom may be $C_1$~$C_{18}$ trialkyl tertiary amine, preferably $C_1$~$C_{12}$ trialkyl tertiary amine, more preferably at least one alkyl therein is $C_1$~$C_6$ alkyl, and the tertiary amine having several N atoms may be: $R_aR_bN(CH_2)_pNR_cR_d$, wherein $R_a$, $R_b$, $R_c$ and $R_d$ may be $C_1$~$C_{18}$ alkyl, preferably $C_1$~$C_{12}$ alkyl, more preferably at least one alkyl therein is $C_1$~$C_6$ alkyl. p is an integer of 1~10, preferably 1~8, more preferably 2~5. Taking into account the steric effect, the chain length of $R_a$, $R_b$, $R_c$ and $R_d$ should be matched with that of methylenes. For the longer chain of methylenes, the chain length of $R_a$, $R_b$, $R_c$ and $R_d$ can not be too long, at least the alkyl linked with one of the nitrogen atoms therein should be shorter; in contrast, for the shorter chain of methylenes, the chain length of the alkyl may be increased correspondingly.

Said organic solvent can make the resin swell, for example, it may be $C_1$~$C_4$ alcohols, dioxane, tetrahydrofuran, etc., and may also be a mixture of several solvents of them. The amount of organic solvent used is 5~20 ml/g bactericide, preferably 10~20 ml/g bactericide based on the weight of the first class of bactericides.

When extracted under reflux, the kind and amount of the organic solvent used can be the same as those of the reaction solvent. After 0.5~2 hrs of extraction, filteration is carried out. The resulting solid after filtered is washed with hot ethanol at 30~75° C. for 1~3 times, the amount of the hot ethanol used for each time is ½~¼ of the amount of the reaction solvent.

The reaction equation of the process said above is:

The carried amount of the quaternary ammonium group in the desired product can be determined through the increased weight of the first class of bactericide as a starting material.

The fourth class of the bactericides according to the invention consists of three parts including a resin carrier, a quaternary ammonium group-containing quaternary phosphonium salt and a quaternary ammonium salt. Its structural formula is as follows:

(IV)

where [P] is the resin which can be chloromethylated, R is $C_4$~$C_{24}$ alkyl, R' is $C_1$~$C_{18}$ alkyl, m is the carried amount of quaternary ammonium group per gram of the bactericide, n is an integer of 2~10, $R_1$, $R_2$ and $R_3$ are $C_1$~$C_8$ alkyl, k is the carried amount of the functional group amino quaternary phosphonium salt per gram of the bactericide, $X^{-a}$ is selected from $Cl^-$, $Br^-$, $I^-$, $NO_3^-$, $SO_4^{2-}$, $CO_3^{2-}$ or $OH^-$, a is the valence of X. Q is an aliphatic tertiary amine. f is the carried amount of the quaternary ammonium salt per gram of the bactericide.

The structural formula of said resin carrier part is:

The resin [P] is preferably a polystyrene resin or a gel or large pore-type resin prepared by copolymerizing styrene and divinylbenzene. The crosslinked degree of the gel-type resin maybe 1~15%, preferably 1~4%; the crosslinked degree of the large pore-type resin may be 1~20%, preferably 1~10%.

The structural formula of said quaternary ammonium group-containing quaternary phosphonium salt part is:

wherein R is $C_4$~$C_{24}$ alkyl, preferably $C_6$~$C_{20}$ alkyl, most preferably $C_6$~$C_{16}$ linear or branch chain alkyl: R' is $C_1$~$C_{18}$ alkyl, preferably $C_1$~$C_{12}$ linear or branch chain alkyl; m is the carried amount of the quaternary ammonium group per gram of the bactericide, which may be 0.1~0.8 mmol/g bactericide, generally 0.1~0.4 mmol/g bactericide is suitable; n is an integer of 2~10, preferably 3~8, most preferably 3~6; $R_1$, $R_2$ and $R_3$ are $C_1$~$C_8$ alkyl, preferably $C_1$~$C_6$ alkyl, most preferably $C_1$~$C_4$ alkyl; $R_1$, $R_2$ and $R_3$ may be same or different; k is the carried amount of the functional group quaternary phosphonium salt per gram of the bactericide, which may be 0.1~1 mmol/g bacericide, generally 0.1~0.4 mmol/g bactericide; the greater k and m values are, the more advantageous it is to increasing the bactericidal activity. However, the m value can not be greater than the k value.

The structural formula of said quaternary ammonium salt part is -$[Q^+]_f \cdot X^{-a}_{f/a}$, wherein Q is an aliphatic tertiary amine, which can be a tertiary amine containing one N atom, and can also be a tertiary amine containing several N atoms. For example, the tertiary amine having one N atom may be $C_1$~$C_{18}$ trialkyl tertiary amine, preferably $C_1$~$C_{12}$ alkyl teriary amine, more preferably at least one alkyl therein is $C_1$~$C_6$ alkyl; the tertiary amine having several N atoms may be: $R_a R_b N(CH_2)_p NR_c R_d$, wherein $R_a$, $R_b$, $R_c$ and $R_d$ may be $C_1$~$C_{18}$ alkyl, preferably $C_1$~$C_{12}$ alkyl, more preferably at least one alkyl therein is $C_1$~$C_6$ alkyl; p is an integer of 1~10, preferably 1~8, more preferably 2~5. Taking into account the steric effect, the chain length of $R_a$, $R_b$, $R_c$ and $R_d$ should be matched with that of methylenes. For the longer chain of methylenes, the chain length of $R_a$, $R_b$, $R_c$ and $R_d$ can not be too long, and at least the alkyl linked with one of the nitrogen atoms therein should be shorter; in contrast, for the shorter chain of methylenes, the chain length of the alkyls may be increased correspondingly. f is the carried amount of the quaternary ammonium salt per gram of bactericide, which may be 0.1~5 mmol/g bactericide, generally 0.4~3.5 mmol/g bactericide is suitable.

Said fourth class of bactericide according to the invention may be prepared on the basis of the third class of bactericide, the particular method is as follows:

Alkyl halide, an organic solvent and the third class of bactericide are mixed, reacted at a temperature of 20~100° C., preferable 40~80° C. for 10~60 hrs, more preferably 30~50 hrs, then the reaction solution is filtered, washed with a solvent for 1~2 times, and dried at a temperature below 100° C.

The structural formula of said alkyl halide is R'Y, where R' is $C_1$~$C_{18}$ alkyl, preferably $C_1$~$C_{12}$ linear or branch chain alkyl; wherein Y is halogen, which may be chlorine, bromine or iodine. The amount of the alkyl halide used is 0.1~3 mmol/g bactericide, preferably 0.1~1 mmol/g bactericide based on the weight of the third class of bactericides.

Said organic solvent is a solvent which can make the third class of bactericides swell, for example, it may be $C_1$~$C_4$ alcohols, dioxane, tetrahydrofuran, benzene, etc., and may also be a mixture of several solvents of them. The amount of organic solvent used is 5~20 ml/g bactericide, preferably 10~20 ml/g bactericide based on the weight of the third class of bactericides.

Said solvent used for washing may be said organic solvent, and also diethyl ether or its mixture with an organic solvent. The amount of the solvent used when washing should be 2~20 times of the product volume, preferably 5~10 times.

The reaction equation of the process said above is:

The amount of the quaternary ammonium group formed by quaternization of R'Y in final product can be determined through the increased weight of the third class of bactericide as a starting material.

After being used, said four classes of bactericides said above according to the present invention can be regenerated by the method as follows: separating the used bactericide from the solution in which the bactericide exists, dipping in the mixed solvent of 4~12 N of hydrochloric acid and anhydrous ethanol with the volume ratio of 1:0.5~3 for 1~3 hrs, filtering, and washing with anhydrous ethanol for 1 ~2 times, then drying at a temperature below 100° C.

The bactericide series according to the invention has excellent bactericidal activity, the bactericidal rate may be up to 100% after 15 minutes. The series of bactericide is water-insoluble, and can be regenerated and reused and widely applied to sterilizing and disinfecting fluid media such as various industrial and domestic water and the like.

The present invention will be illustrated further by the following example, but not limited therefrom.

The chloromethylated resin (hereafter called as chlorosphere) used in the following examples is prepared by chloromethylating the whitesphere available from market (wherein the whitesphere is prepared by copolymerizing styrene and divinylbenzene). The chloromethylation method is as follows: adding 10 g of whitesphere which meets the requirement of crosslinked degree, 20~40 ml of chloromethyl ether and 20 ~40 ml of anhydrous dichloromethane in a reaction flask; swelling the mixture at room temperature under stirring for 20 ~30 min; cooling to below 0° C.; then adding in bacthes 10~50 ml of a solution having a concentration of 0.2~0.6 g AlCl$_3$/ml nitrobenzene in the reaction flask, maintaining the reaction temperature not higher than 0° C. by adjusting the addition rate, then adding dropwise the mixed solution of 6N HCl and dioxane with the volume ratio of 1:1 under stirring after the reaction is finished; and then filtering the resulting mixture, washing and drying. The specific method can be seen in (*Ionexchange resin*), Edited by R. Koning, (translated by Zu Xiuchang et al., Academy Press, 1966).

Other starting materials and agents used in the examples of the invention are commercial products.

EXAMPLE 1

This example involves the preparation of γ-chloropropyl tributyl phosphonium bromide.

In a 500 ml three-neck flask, 267 g (1.7 mol) of γ-bromo-1-chloropropane (BrCH$_2$CH$_2$CH$_2$Cl) (CP grade, from Beijing Chemical Agent Corp.) was cooled in a ice-salt bath to a temperature below 0° C., and then 202 g (1 mol) of tributyl phosphine (available from Beijing Xing Hua Water Stablizer Factory) was rapidly added dropwise within 12 hrs under stirring while the process temperature was maintained at a temperature not higher than 5° C. Then the temperature rose naturaly to room temperature under stirring. The reaction was contiuously carried out with stirring under the room temperature for 48 hrs to form a great quantity of white solid in the flask; 200 ml of diethyl ether was added to separate more products, filtered, and washed with diethyl ether; 302 g of the crude product was obtained in a yield of about 85% (based on PBu$_3$), and then recrystallized with 3000 ml of the mixed solvent of CH$_2$Cl$_2$ and diethyl ether (volume ratio 1:1), the recrystallized product was dried at 80° C.

Figure 1:
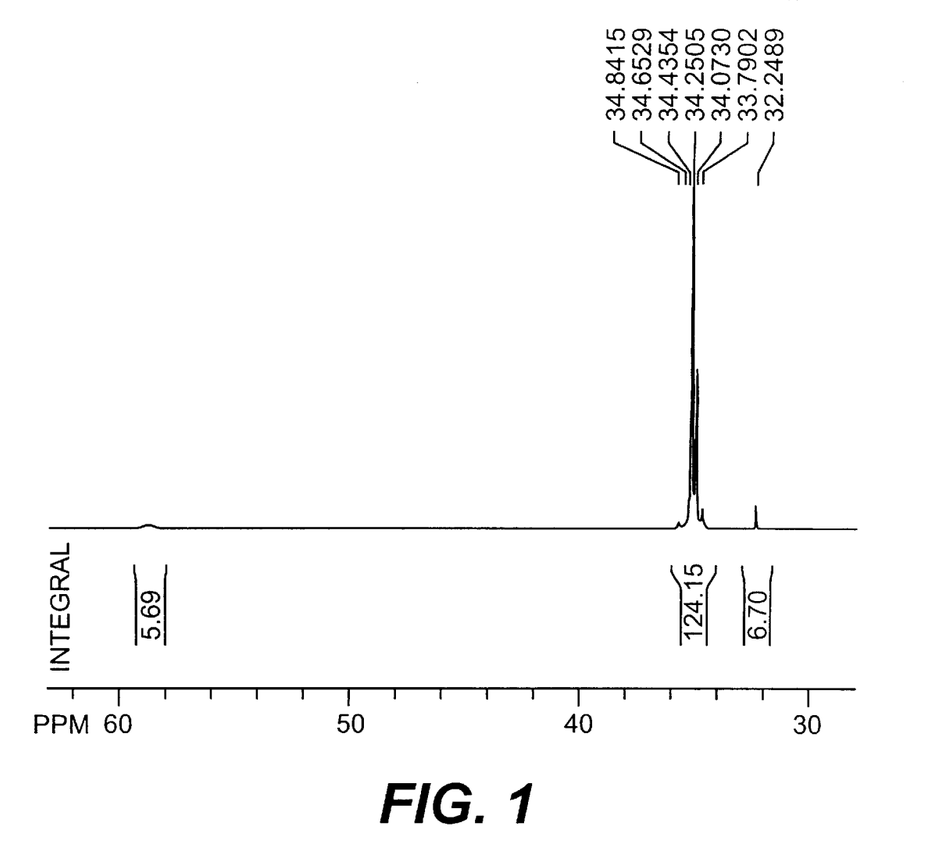
FIG. 1 shows the $^{31}$PNMR(solid) spectrogram of Y-chloropropyl tributyl phosphonium bromide.
Figure 2:
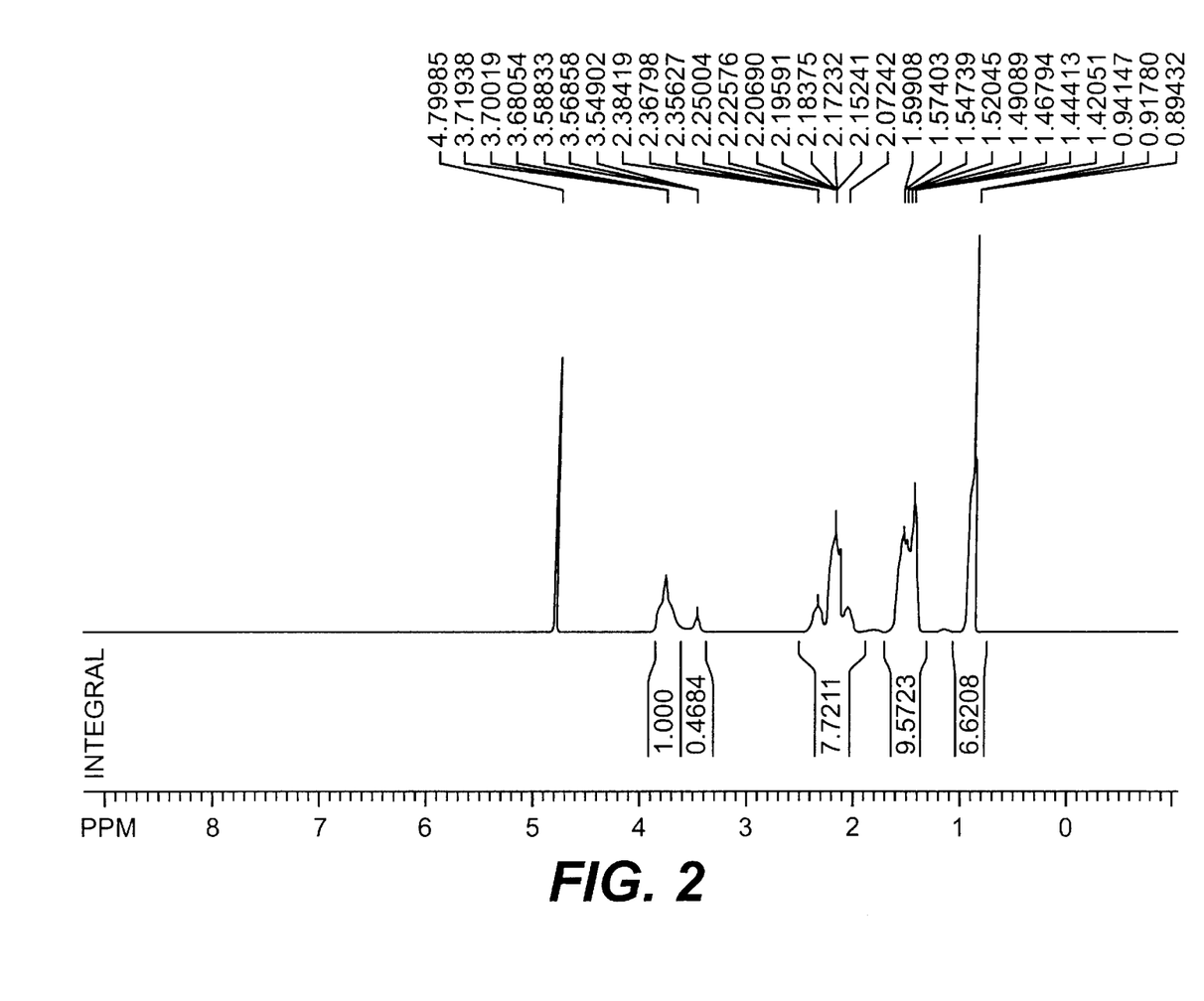
FIG. 2 shows the HNMR(CDCl$_3$) spectrogram of Y-chloropropyl tributyl phosphonium bromide.

The product was analysed based on the $^{31}$PNMR and HNMR spectrogram (see in FIG. 1 and FIG. 2). In FIG. 1 the characteristic peak at about 34.2505 ppm shows the existence of the quaternary phosphonium. In FIG. 2, the peaks are assigned as follows:

XCH$_2{}^a$CH$_2{}^b$CH$_2{}^b$P$^+$(CH$_2{}^b$CH$_2{}^c$CH$_2{}^c$CH$_3{}^d$)$_3$, 3.72~3.68 ppm (triplet, H$^a$, X=Cl); 3.59~3.55 ppm (triplet, H$^a$, X=Br); the content ratio of X=Cl and X=Br is 2.1:1; 3.72~3.55 (2H$^a$); 2.38~2.07 ppm (two triplets, one multiplet 10H$^b$), 1.6~1.42 ppm (two multiplets, 12H$^c$); 0.94~0.89ppm (one triplet, 9H$^d$).

EXAMPLE 2

This example involves the preparation of ε-bromo hexyl triethyl phosphonium bromide.

In a 100 ml three-neck flask, 8.8 g (0.075 mol) of triethyl phosphine and 26.0 g (0.107 mol) of 1.6-dibromohexane (Beijing Chemical Agent Corp.) were added, N$_2$ of about 1 atm was introduced, then the flask was sealed and heated to 75±3° C., the reaction was carried out with stirring for 30 hrs, then cooled to room temperature after the reaction was completed, and 20 ml of diethyl, ether was added to separate a great quantity of white solid, then filtered, and washed with diethyl ether, 24 g of white solid was then obtained in a yield of about 90%, then the resulting solid was recrystallized from 240 ml of a mixed solvent of chloroform and diethyl ether (volume ratio 1:1), and the product obtained was dried at the temperature of 80° C.

EXAMPLE 3

This example involves the preparation of ε hexylamino-hexyl triethyl phosphonium bromide, of which the structural formula is:

CH$_3$(CH$_2$)$_5$ NH(CH$_2$)$_6$P$^+$(C$_2$H$_5$)$_3$Br$^-$.

In a 250 ml of three-neck flask, 10.5 g of n hexamine (about 0.1 mol), 40 ml of anhydrous ethanol and 14.0 g anhydrous K$_2$CO$_3$ (ground) were added, heated to reflux, 60 ml of an ethanol solution of ε-bromohexyl triethyl phosphonium bromide (of which 25.2 g of ε-bromohexyl triethyl phosphonium bromide was dissolved previously in about 60 ml ethanol) was then added dropwise within 6 hrs while stirring and reflux, and then reacted for 2 hrs while stirring and reflux, when the reaction was ended, the inorganic salt was filtered out while the solution was hot, and the solvent was distilled off, then the residue was cooled to room temperature, 150 ml of diethyl ether was then added to the residue to separate a large quantity of white solid, then filtered, and the crude product as white solid was obtained. The crude product was recrystallized from the mixed solvent of $CH_2Cl_2$ and diethyl ether (volume ratio 1:1) to carry out purification, then the resulting white solid was filtered, and washed with 30 ml diethyl ether twice, then dried at 80° C.

EXAMPLE 4

The procedure of example 3 was repeated only by substituting 13.4 g of n-octylamine (CP grade, Beijing Chemical Factory) for 10.5 g n-hexamine, the ε octylaminohexyl triethyl phosphonium bromide having the structural formula was obtained:

$C_8H_{17}NH(CH_2)_6P^+(C_2H_5)_3Br^-$.

EXAMPLE 5

The procedure of example 4 was repeated only by substituting the γ-chloropropyl tributyl phosphonium bromide (25.2 g phosphonium bromide was dissolved previously in 60 ml ethanol) for the ε-bromohexyl triethyl phosphonium bromide, the γ-n-octylamino-propyl tributyl phosphonium bromide having the strucural formula was obtained:

n-$C_8H_{17}NH(CH_2)_3P^+(C_4H_9)_3$ $Br^-$.

EXAMPLE 6

The procedure of example 5 was repeated only by substituting 16.3 g n-decylamine for 10.5 g n-octylamine, the γ-n-decylaminopropyl tributyl phosphonium bromide having the structural formula was obtained:

n-$C_{10}H_{21}NH(CH_2)_3P^+(C_4H_9)_3Br^-$.

EXAMPLE 7

In a 100 ml of reaction flask, 9.30g of n-dodecylamine (about 0.05 mol) (Tianjin Kelong Chemical Agent Factory, CP Grade) was added, and dissolved by adding 25 ml of dioxane under stirring, then 25 ml of anhydrous ethanol and 7.0 g anhydrous $K_2CO_3$ (ground) were added, heated to reflux, and 30 ml of an ethanol solution of 13 g (about 0.035 mol) of γ-chloropropyl tributyl phosphonium bromide (13 g of γ-chloropropyl tributyl phosphonium bromide was dissolved previously in 30 ml ethanol) was then added dropwise within 6 hrs under stirring and reflux, then again reacted for 2hrs under stirring and reflux, when the reaction was ended, the inorganic salt was filtered out while the solution was hot, and the solvent was distilled off from the filtrate, then the residue was cooled to room temperature, then 100 ml of diethyl ether was added to separate a large quantity of white solid, and filtered, the crude product was then obtained. The crude product was recrystallized from the mixed solvent of tetrahydrofuran and diethyl ether (volume ratio 1:1) for purification, the γ n-dodecylamino-propyl tributyl phosphonium bromide having the structural formula was then obtained: n-$C_{12}H_{25}NH(CH_2)_3P^+(C_4H_9)_3$ $Br^-$.

Figure 3:
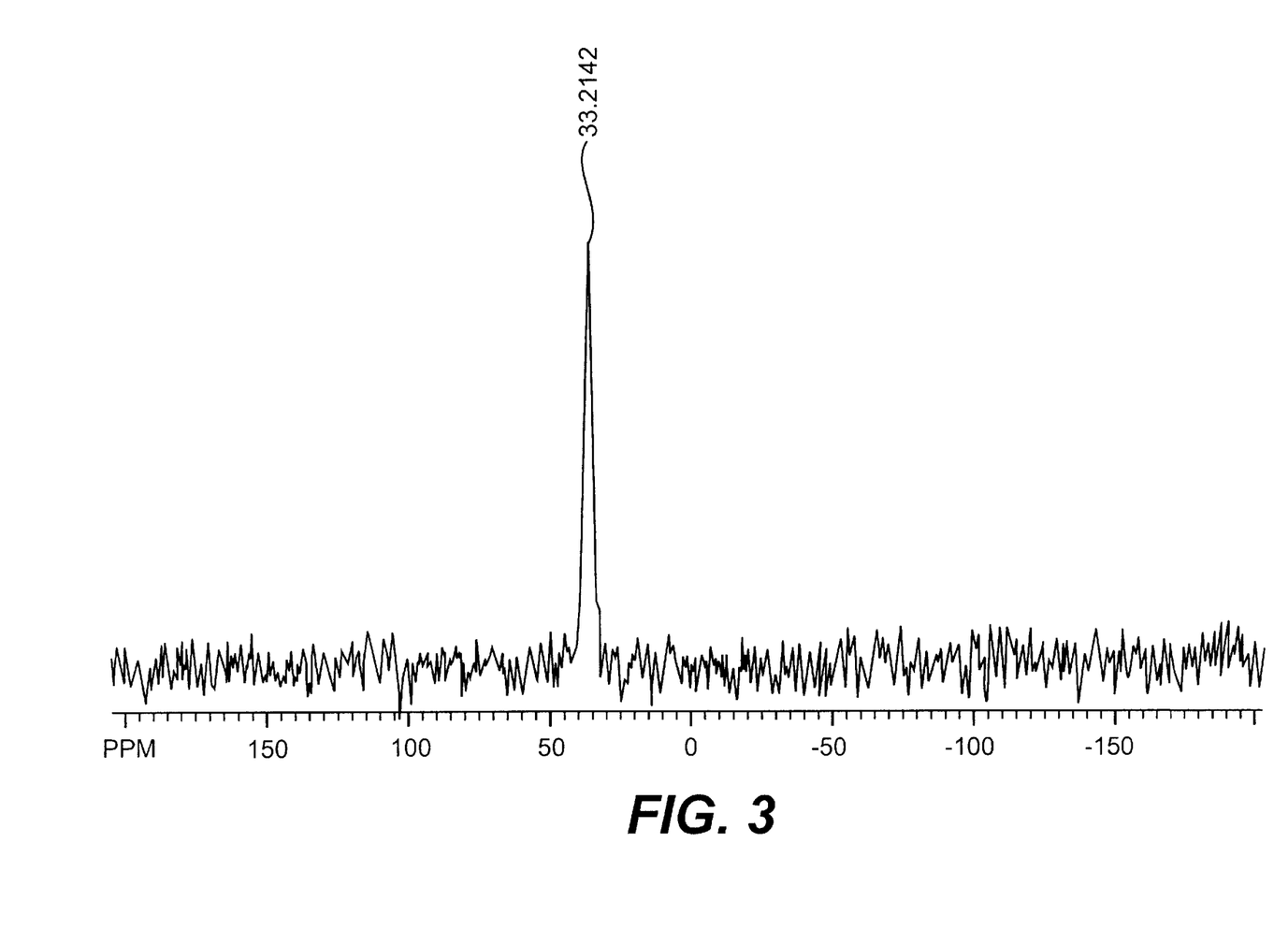
FIG. 3 shows the $^{31}$PNMR(solid) spectrogram of dodecylamino propyl tributyl phosphonium bromide.

In FIG. 3, the characteristic peak at about 33.2142 ppm shows the existence of the quaternary phosphonium, compared with FIG. 1, a displacement of the peaks occurs, showing the environment of P changes due to the reaction occurrence.

EXAMPLE 8

The procedure of Example 7 was repeated only by substituting 10.7 g of n-tetradecylamine for 9.30 g of n-dodecylamine, the γ-n-tetradecylamino-propyl tributyl phosphonium bromide having the structural formula was obtained:

n-$C_{14}H_{29}NH(CH_2)_3P^+(C_4H_9)_3Br^-$.

EXAMPLE 9

The procedure of Example 7 was repeated only by substituting 12 1g of hexadecylamine for 9.30 g of n-dodecylamine, the γ-n-hexadecylamino-propyl tributyl phosphonium bromide having the structural formula was obtained:

n-$C_{16}H_{33}NH(CH_2)_3P^+(C_4H_9)_3Br^-$.

EXAMPLE 10–16

These examples provide the preparation of the first class of bactericides according to the present invention, which consists of the amino quaternary phosphonium salt as an active bactericidal component carried on a resin carrier.

Upon the amounts used in Table 1, 5.00 g of chloromethlated copolymer resin of styrene and divinylbenzene (called abbreviately as chloroshphere in the table) was added to a reaction solvent and made swell at room temperature for 1 h, one amino quaternary phosphonium selected from the amino quaternary phosphoniums of example 3–9 mentioned above was added and reacted under stirring and reflux. After the reaction was completed, the reaction solution was heated to reflux and extracted with a solvent having the same name and amount as that of the reaction solvent for 1 hr, and filtered, washed successively with hot ethanol, hot water and hot ethanol each having a temperature of 60° C. twice, the amount of the washing liquid used for each time was ⅓ of the amount of the reaction solvent used. Eventually, the washing solution was filtered, the resulting solid was dried at a temperature below 100° C. The carried amount of the amino quaternary phosphonium salt per gram of polymeric amino quaternary phosphonium salt can be calculated by the increased weight of the chlorosphere.

TABLE 1

| | Examples | 10 | 11 | 12 | 13 | 14 | 15 | 16 |
|---|---|---|---|---|---|---|---|---|
| Chloro-Sphere | Form | gel | gel | gel | L. pore | L. pore | L. pore | gel |
| | Crosslinked degree, % | 1 | 1 | 2 | 10 | 4 | 4 | 1 |
| | Chlorine content, % | 22 | 22 | 16 | 12 | 20 | 20 | 22 |
| | Amount used, g | 5.00 | 5.00 | 5.00 | 5.00 | 5.00 | 5.00 | 5.00 |

TABLE 1-continued

| Examples | | 10 | 11 | 12 | 13 | 14 | 15 | 16 |
|---|---|---|---|---|---|---|---|---|
| AQPS | Example No. it is Selected from | 7 | 8 | 5 | 3 | 4 | 9 | 6 |
| | Amount used, g | 6.3 | 5.0 | 6.1 | 4.3 | 6.1 | 3.2 | 11.9 |
| Solvent | Name | DX + EA | DX + EA | EA | THF | THF + EA | DX | DX + EA |
| | Amount used, ml | 50 + 20 | 40 + 20 | 50 | 60 | 40 + 40 | 50 | 40 + 60 |
| Reaction time, h | | 60 | 72 | 48 | 48 | 12 | 60 | 32 |
| Weight of product, g | | 5.57 | 5.50 | 5.57 | 5.22 | 5.45 | 5.60 | 5.81 |
| Carried amount of AQPS, mmol/g bactericide | | 0.258 | 0.170 | 0.226 | 0.151 | 0.268 | 0.191 | 0.290 |

Figure 4:
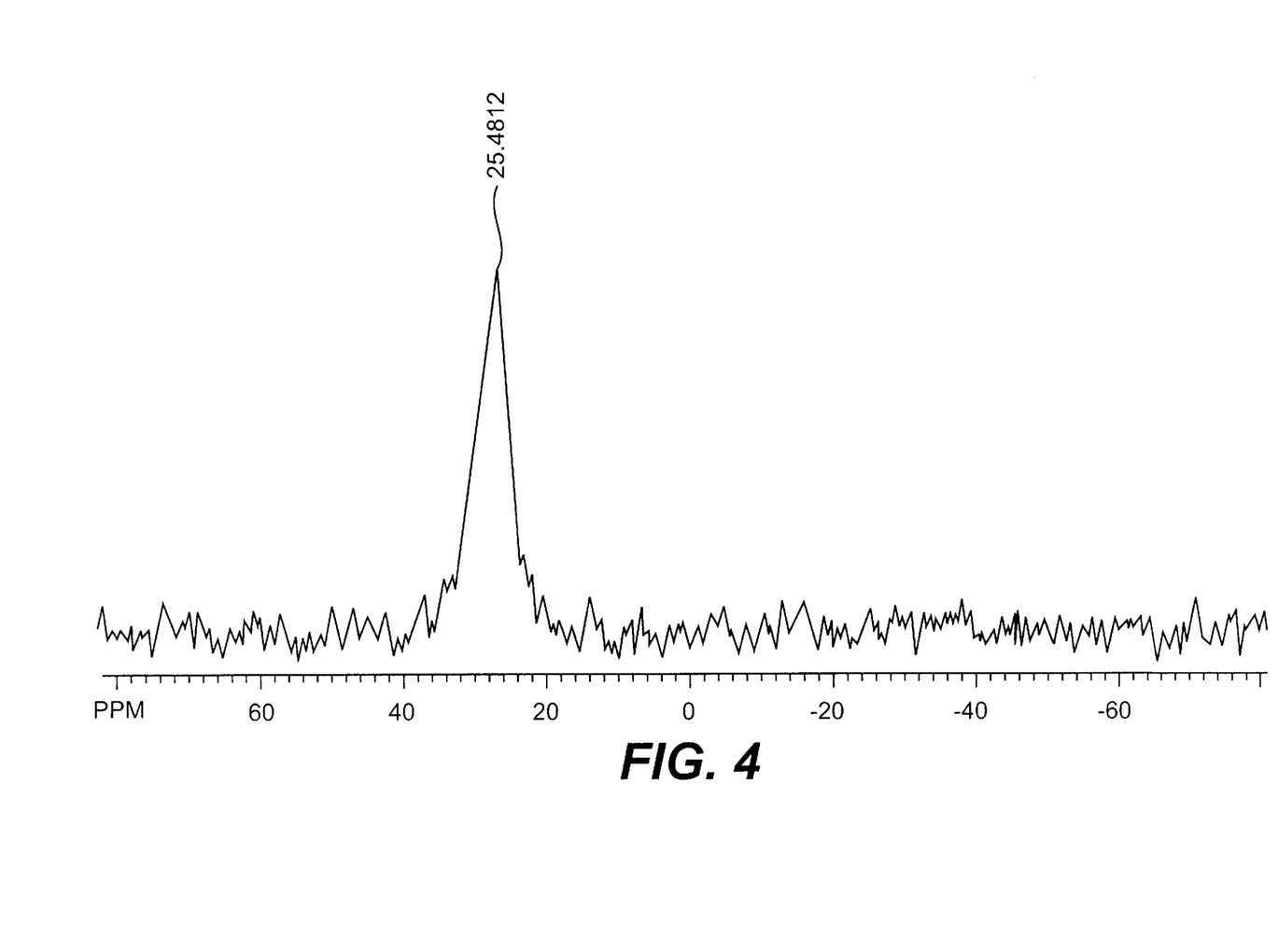
FIG. 4 shows the $^{31}$PNMR(solid) spectrogram of a water-insoluble polymer of the dodecylaminopropyl tributyl phosphonium bromide.
Figure 5:
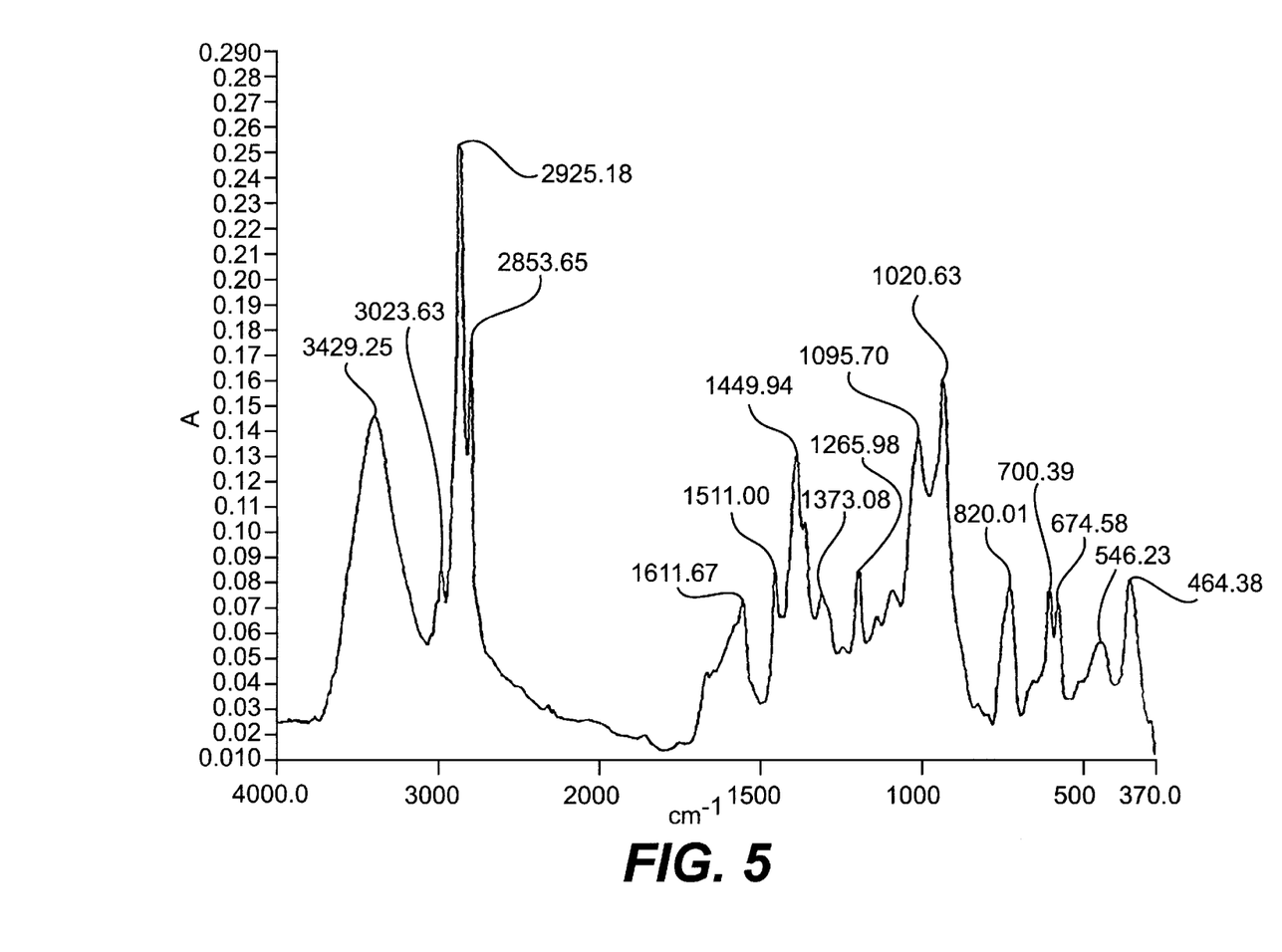
FIG. 5 shows the IR spectrogram of a water-insoluble polymer of the dodecylaminopropyl tributyl phosphonium bromide.

Notes: AQPS: Amino quaternary Phosphonium salt; DX: dioxane; EA: ethanol; THF: Tetrahydrofuran: L. pore: Large pore The spectrogram of the polymeric quaternary phosphonium salt of example 10 was analyzed. In FIG. 4, the charateristic peak at 25.4812 ppm shows that the functional group quaternary phosphonium salt exists, compared with FIG. 3, the displacement of peak occurs significantly, and proves that the carrying reaction take places. In FIG. 5, the absorption peak at 3429.05 cm$^{-1}$ is from stretching vibration of N—H, the absorption peak at 1373.08 cm$^{-1}$ is the characteristic peak of $CH_3$, showing that the amino quaternary phosphonium salt has been carried on the resin.

EXAMPLE 17–23

These examples provide the preparation of the second class of bactericides according to the present invention, which consists of, as an active bactericidal component, the quaternary ammonium group-containing quaternary phosphonium salt carried on the resin carrier.

Upon the amounts used shown in Table 2, one of the first class of bactericide selected from those of examples 10–16 was added to a certain amount of a reaction solvent and iodomethane, and reacted at 40~45° C. for a certain period of time under stirring, then filtered, and washed successively with ethanol, water and ethanol twice respectively, the amount of washing liquid used for each time is ⅓ of that of the reaction solvent, then filtered, and dried at the temperature below 100° C. The carried amount of the quaternary ammonium group and the quaternary phosphonium salt per gram of the second class of bactericide can be calculated by the increased weight of the first class of bactericide as a starting material.

TABLE 2

| Example | | 17 | 18 | 19 | 20 | 21 | 22 | 23 |
|---|---|---|---|---|---|---|---|---|
| First class bactericide | Example No. it is selected from | 10 | 11 | 12 | 13 | 14 | 15 | 16 |
| | Amount used, g | 5.00 | 5.00 | 5.00 | 5.00 | 5.00 | 5.00 | 5.00 |
| Reaction solvent | Name | DX | THF | DX + THF | EA | THF + EA | DX | THF |
| | amount used, ml | 80 | 60 | 20 + 30 | 80 | 30 + 50 | 70 | 100 |
| $CH_3I$ amount used, g | | 5.0 | 1.0 | 6.0 | 3.0 | 6.0 | 5.0 | 6.0 |
| Reaction time, h | | 48 | 36 | 36 | 48 | 48 | 36 | 36 |
| Reaction temperature, ° C. | | 35 | 40 | 45 | 50 | 45 | 40 | 55 |
| Produt weight, g | | 5.18 | 5.12 | 5.16 | 5.10 | 5.19 | 5.13 | 5.20 |
| Carried amount of QAmG per gram of the product bactericide, mmol/g bacreicide | | 0.245 | 0.165 | 0.218 | 0.138 | 0.258 | 0.178 | 0.271 |
| Carried amount of QPhS per gram of the product bactericide, mmol/g bacreicide | | 0.249 | 0.166 | 0.219 | 0.148 | 0.255 | 0.186 | 0.279 |

Notes: DX: dioxane; EA: ethanol; THF: Tetrahydrofuran; QPhS: Quaternary Phosphonium Salt, QAmG: Quaternary Ammonium Group.

EXAMPLE 24–31

These examples provide the preparation of the third class of bactericides according to the present invention, which consists of, as an active bactericidal component, the amino quaternary phosphonium salt and quaternary ammonium salt carried on the resin carrier.

Upon the amount used shown in Table 3, one of the first class of bactericide selected from those of examples 10–16 was added to a certain amount of a reaction solvent and a tertiary amine, and reacted for a certain period of time under stirring, and filtered, washed successively with ethanol, water and ethanol twice respectively, the amount of the washing liquid for each time is ⅓ of that of the reaction solvent, then filtered and dried at a temperature below 100° C. The carried amount of the quaternary ammonium group and the quaternary phosphonium salt per gram of the third class of bactericide can be calculated by the increased weight of the first class bactericide as a starting material.

TABLE 3

| Example | | 24 | 25 | 26 | 27 | 28 | 29 | 30 | 31 |
|---|---|---|---|---|---|---|---|---|---|
| First class bactericide | Example No. it selected from. | 10 | 10 | 11 | 12 | 13 | 14 | 15 | 16 |
| | Amount used, g | 5.00 | 5.00 | 5.00 | 5.00 | 5.00 | 5.00 | 5.00 | 5.00 |
| Reaction solvent | Name | DX + EA | B | THF + EA | THF | EA | EA | DX | EA |
| | Amount used, ml | 40 + 40 | 100 | 40 + 20 | 70 | 80 | 60 | 100 | 80 |
| Organic Tertiary Amine | Name | TEA | TMEDA | TEA | TEA | TEA | TEA | TEA | TEA |
| | Amount used, g | 2.0 | 5.0 | 2.0 | 2.0 | 2.0 | 2.0 | 2.0 | 2.0 |
| Reaction time, h | | 48 | 36 | 48 | 24 | 48 | 48 | 48 | 48 |
| Produt weight, g | | 5.33 | 7.78 | 5.80 | 5.42 | 5.24 | 6.02 | 6.10 | 5.40 |
| Carried amount of QAmG per gram of the product bactericide, mmol/g bacreicide | | 0.613 | 3.08 | 1.37 | 0.767 | 0.453 | 1.68 | 1.79 | 0.733 |
| Carried amount of QPhS per gram of the product bactericide, mmol/g bacreicide | | 0.242 | 0.166 | 0.147 | 0.208 | 0.144 | 0.223 | 0.157 | 0.269 |

Notes: DX: dioxane; EA: ethanol; THF: Tetrahydrofuran; QPhS: Quaternary Phosphonium Salt, QAmG: Quaternary Ammonium Group, B: benzene: TEA: triethyl amine; TMEDA: tetra methyl ethylene diamine, of formula: $(CH_3)_2N(CH_2)_2N(CH_3)_2$.

EXAMPLE 32–39

These examples provide the preparation of the fourth class of bactericides according to the present invention, which consists of, as an active bactericidal component the quaternary ammonium group-containing quaternary phosphonium salt and quaternary ammonium salt carried on the resin carrier.

Upon the amounts used shown in Table 4, one of the third class of bactericide selected from those of examples 24–31 was added to a certain amount of a reaction solvent and iodomethane, and reacted at 40–45° C. for a certain period of time under stirring, then filtered, washed successively with ethanol, water and ethanol twice respectively, the amount of the washing solvent used for each time is ⅓ of that of the reaction solvent used, then filtered, and dried at the temperature below 100° C. The carried amount of the quaternary ammonium group contributed by quaternisation with iodomethane per gram of the fourth class of bactericide can be calculated by the increased weight of the third class of bactericide as a starting material, and also the total carried amount of the quaternary ammonium group in the product, and then the carried amount of the quaternary phosphonium salt can be obtained therefrom.

TABLE 4

| Example | | 32 | 33 | 34 | 35 | 36 | 37 | 38 | 39 |
|---|---|---|---|---|---|---|---|---|---|
| Third class bactericide | Example No. it is selected from | 24 | 25 | 26 | 27 | 28 | 29 | 30 | 31 |
| | Aamount used, g | 5.00 | 5.00 | 5.00 | 5.00 | 5.00 | 5.00 | 5.00 | 5.00 |
| Reaction solvent | Name | DX | EA + DX | THF | EA | THF + EA | THF + DX | DX | THF |
| | Amount used, ml | 80 | 70 + 30 | 60 | 50 | 30 + 30 | 30 + 40 | 70 | 80 |
| $CH_3I$ amount used g | | 3.0 | 6.0 | 2.0 | 3.0 | 6.0 | 5.0 | 4.0 | 4.0 |
| Reaction time, h | | 36 | 48 | 36 | 36 | 60 | 36 | 48 | 48 |
| Product weight, g | | 5.17 | 7.00 | 5.10 | 5.14 | 5.10 | 5.16 | 5.11 | 5.19 |
| Reaction quantity of quaternisation of $CH_3I$, mmol/g bactericide | | 0.232 | 2.012 | 0.138 | 0.192 | 0.138 | 0.218 | 0.152 | 0.258 |
| Total carried amount of QAmG in product, mmol/g bactericide | | 0.825 | 4.212 | 1.481 | 0.938 | 0.582 | 1.846 | 1.903 | 0.964 |
| Carried amount of QPhS in product, mmol/g bactericide | | 0.235 | 0.119 | 0.144 | 0.202 | 0.141 | 0.215 | 0.154 | 0.259 |

Notes: DX: dioxane; EA: ethnol; THF: Tetrahydrofuran; QPhS: Quaternary Phosphonium Salt, QAmG: Quaternary Ammonium Group.

EXAMPLE 40

This example is for evaluation of bacteticidal activity.

Since the bacteria existing in cooling water of industrial recirculation are mainly heterotrophic bacteria such as acinetobacter, pseudomonas, enterobacterium, etc., the bacteria suspension prepared by the strains containing different heterotrophic bacteria is used during the evaluation of the samples of the invention.

The method for evaluating bactericidal activity is as follows:

1. Culture of strains

The strain for test was cultured on a slant culture medium for 72 hrs, the medium was prepared by: heating and dissolving 15 g of agar with distilled water, then adding sequentially 10 g of peptone, 3 g of beef extract, 5 g of NaCl, then stirring and mixing them homogenously, and adding distilled water to make the liquid volume upto 1 liter, adjusting the pH to about 7.5 with solutions of 1M HCl and 1M NaOH, and then packed dividedly while the resulting mixture was still hot, and then sterilizing at 121° C. with high pressure steam for 30 minutes, pH value was 7.2~7.4 after sterlized.

2. Preparation of the bacteria suspension

The strain which was incubated and cultured for 72 hrs was transferred into a conical flask with the sterlized physiological saline, the resulting solution was shaked thoroughly to disperse bacteria pellet fully in the phsiological saline, then diluted to a concentration of $10^{3-10^{11}}$ bacteria/ml of bacteria suspension with the sterilized water.

3. Evaluation method

In a 150 ml conical flask, 50 mg of each of various bactericides according to the invention was fed, then 50 ml the bacteria suspension was added. The contents were shaken for 15 minutes and then was set still. After 1 ml of the treated bacteria suspension was gradient diluted, 1 ml of the diluted suspension was taken and put in a culture dish, then a culture medium which was melted and cooled to about 40° C. was added thereto. The mixture was shaken homogeneously, and then cultured at 30° C. for 72 hrs. Finally, the survival bacterium number and bactericidal rate were calculated.

$$\text{Bactericidal rate } \% = \frac{\text{Initial bacterium number} - \text{Survival bacterium number}}{\text{Initial bacterium number}} \times 100\%$$

The specific method can be seen in the reference of Feng jun's "Microorganism Analysis in Industrial Water Treatment" (Guang Dong Science & Technique Publishing, 1985).

The evaluation results of the bactericidal activity of the first, second and third class of bactericides according to the present invention are shown in Tables 5, 6 and 7 respectively. The test strains shown in the Tables are: acinetobacter calcoaceticus, staphylococcus aureus, alcaligenes faecalis, pseudomonas mendocina, aeromonas hydrophila, enterobacter aerogenes, citrobacter freundii.

In Table 8 and Table 9, the evaluation results of the bactericidal activity of the first and fourth class of bactericides according to the invention are shown respectively. The test strains in these tables are: pseudomonas stutzeri, pseudomonas mendocina, pseudomonas aeruginosa, enterobacter aerogenes, citrobacter freundii.

As shown from Table 5 to Table 9, all the various water-insoluble polymeric quaternary phosphonium salt type bactericides according to the present invention have a rapid and high effective bactericidal activity to various heterotrophic bacteria, thus they can be used widely for sterilizing and disinfecting fluid media such as different industrial and domestic water and the like.

EXAMPLE 41

This example is the evaluation of bactericidal properties of the bactericides which have been regenerated once.

After being used, the bactericide of example 10 was filtered, separated, and dipped in a mixed solvent of 6N hydrochloric acid and anhydrous ethanol having volume ratio of 1: 3 for 3 hrs, then filtered and washed twice with ethanol, and dried at a temperature below 100° C., and then used for the evaluation of bactericidal activity accoding to the method of example 40, the test strains used in the test were same as those of the tests shown in Table 5 - Table 7, the treatment time was 15 minutes, initial bacterium number was $2.7 \times 10^9$ bacteria/ml, and survival bacterium number was $1.3 \times 10^6$ bacteria/ml. So the bactericidal rate was 99.94% and the survival rate was 0.06%.

This example shows that the bactericides according to the invention, after being regenerated, still have excellent bactericidal activity. Therefore they can be reused repeatedly.

TABLE 5

| Example No. from which Bactericide is selected | 10 | 11 | 12 | 13 | 14 | 15 | 16 |
|---|---|---|---|---|---|---|---|
| Bactericide amount used, mg/ml | 1.0 | 1.0 | 1.0 | 1.0 | 1.0 | 1.0 | 1.0 |
| Amount of active bactercidal functional group QPhs in 1 mg amount used, μmol. | 0.258 | 0.170 | 0.226 | 0.151 | 0.268 | 0.191 | 0.290 |
| Initial bacterium number × 10⁹ bacteria/ml | 2.9 | 2.9 | 2.9 | 2.9 | 2.9 | 2.9 | 2.9 |
| Survival bacterium number. bacteria/ml | 0 | $2.0 \times 10^8$ | $9.6 \times 10^4$ | $8.7 \times 10^7$ | $2.2 \times 10^4$ | $1.6 \times 10^8$ | 0 |
| Bactericidal rate, % | 100 | 93.1 | 99.997 | 97 | 99.9992 | 94.5 | 100 |
| Survival rate, % | 0 | 6.9 | 0.003 | 3.0 | 0.0008 | 5.5 | 0 |

TABLE 6

| Example No. from which Bactericide is selected | 17 | 18 | 19 | 20 | 21 | 22 | 23 |
|---|---|---|---|---|---|---|---|
| Bactericide amount used, mg/ml | 1.0 | 1.0 | 1.0 | 1.0 | 1.0 | 1.0 | 1.0 |
| Total amount of QAmG in 1 mg amount used, μmol | 0.245 | 0.165 | 0.218 | 0.138 | 0.258 | 0.178 | 0.271 |
| Amount of active bactericidal | 0.249 | 0.166 | 0.219 | 0.148 | 0.258 | 0.186 | 0.279 |

TABLE 6-continued

| Example No. from which Bactericide is selected | 17 | 18 | 19 | 20 | 21 | 22 | 23 |
|---|---|---|---|---|---|---|---|
| functional group QPhs in 1 mg amount used, μmol. | | | | | | | |
| Initial bacterium number × $10^3$, bacteria/ml | 2.9 | 2.9 | 2.9 | 2.9 | 2.9 | 2.9 | 2.9 |
| Survival bacterium number, bacteria/ml | 0 | $8.0 \times 10^7$ | $4.1 \times 10^4$ | $6.0 \times 10^6$ | $1.0 \times 10^4$ | $7.6 \times 10^7$ | 0 |
| Bactericidal rate, % | 100 | 97.24 | 99.999 | 99.79 | 99.9997 | 97.4 | 100 |
| Survival rate, % | 0 | 2.76 | 0.001 | 0.21 | 0.0003 | 2.6 | 0 |

TABLE 7

| Example No. From which bactericide is selected | 24 | 25 | 26 | 27 | 28 | 29 | 30 | 31 |
|---|---|---|---|---|---|---|---|---|
| Bactericide amount used, mg/ml | 1.0 | 1.0 | 1.0 | 1.0 | 1.0 | 1.0 | 1.0 | 1.0 |
| Total amount of QAmG in 1 mg amount used, μmol | 0.613 | 3.08 | 1.37 | 0.767 | 0.453 | 1.68 | 1.79 | 0.733 |
| Amount of active bactericidal functional group QPhS in 1 mg amount used, μmol. | 0.242 | 0.166 | 0.147 | 0.208 | 0.144 | 0.223 | 0.157 | 0.269 |
| Initial bacterium number × $10^9$ bacteria/ml | 2.9 | 2.9 | 2.9 | 2.9 | 2.9 | 2.9 | 2.9 | 2.9 |
| Survival bacterium number, bacteria/ml | 0 | 0 | 0 | 0 | $4.2 \times 10^5$ | 0 | $2.0 \times 10^5$ | 0 |
| Bactericidal rate, % | 100 | 100 | 100 | 100 | 99.986 | 100 | 99.993 | 100 |
| Survival rate, % | 0 | 0 | 0 | 0 | 0.014 | 0 | 0.007 | 0 |

TABLE 8

| Example No. from which bactericide is selected | 10 | 11 | 12 | 13 | 14 | 15 | 16 |
|---|---|---|---|---|---|---|---|
| Bactericide amount used, mg/ml | 1.0 | 1.0 | 1.0 | 1.0 | 1.0 | 1.0 | 1.0 |
| Amount of active bactericidal functional group QPhS in 1 mg amount used, μmol. | 0.258 | 0.170 | 0.226 | 0.151 | 0.268 | 0.191 | 0.290 |
| Initial bacterium number × $10^9$, bacteria/ml | 8.3 | 8.3 | 8.3 | 8.3 | 8.3 | 8.3 | 8.3 |
| Survival bacterium number, bacteria/ml | $3.7 \times 10^7$ | $5.0 \times 10^5$ | $4.5 \times 10^8$ | $2.2 \times 10^9$ | $5.1 \times 10^7$ | $7.1 \times 10^9$ | $2.1 \times 10^7$ |
| Bactericidal rate, % | 99.955 | 94.0 | 99.46 | 97.35 | 99.94 | 91.4 | 99.975 |
| Survival rate, % | 0.045 | 6.0 | 0.54 | 2.65 | 0.06 | 8.6 | 0.025 |

TABLE 9

| Example No. from which Bactericide is selected | 32 | 33 | 34 | 35 | 36 | 37 | 38 | 39 |
|---|---|---|---|---|---|---|---|---|
| Bactericide amount used, mg/ml | 1.0 | 1.0 | 1.0 | 1.0 | 1.0 | 1.0 | 1.0 | 1.0 |
| Total amount of QAmG in 1 mg amount used, μmol | 0.825 | 4.212 | 1.481 | 0.938 | 0.582 | 1.846 | 1.903 | 0.964 |
| Amount of active | 0.235 | 0.119 | 0.144 | 0.202 | 0.141 | 0.216 | 0.154 | 0.259 |

TABLE 9-continued

| Example No. from which Bactericide is selected | 32 | 33 | 34 | 35 | 36 | 37 | 38 | 39 |
|---|---|---|---|---|---|---|---|---|
| bactericidal functional group QPhs in 1 mg amount used, $\mu$mol. | 8.3 | 8.3 | 8.3 | 8.3 | 8.3 | 8.3 | 8.3 | 8.3 |
| Initial bacterium number × $10^9$ bacteria/ml | | | | | | | | |
| Survival bacterium number, bacteria/ml | 5.2 × $10^5$ | 3.1 × $10^6$ | 7.4 × $10^6$ | 6.8 × $10^6$ | 9.6 × $10^6$ | 6.4 × $10^6$ | 6.2 × $10^5$ | 7.0 × $10^4$ |
| Bactericidal rate, % | 99.9994 | 99.62 | 99.991 | 99.992 | 99.99 | 99.9992 | 99.993 | 99.9999 |
| Survival rate, % | 0.0006 | 0.38 | 0.009 | 0.008 | 0.01 | 0.0008 | 0.007 | 0.0001 |

What is claimed is:

1. A water-insoluble polymeric quaternary phosphonium bactericide, comprising one of the following structures:

where [P] is a resin which can be chloromethylated, R is $C_4$–$C_{24}$ alkyl, R' is $C_1$–$C_{18}$ alkyl, m is 0.1–0.8 mmol/g bactericide, n is an integer of 2–10, $R_1$, $R_2$ and $R_3$ are $C_1$–$C_8$ alkyl, $X^{-a}$ is an anion, a is the valence of X k is 0.1–1 mmol/g bactericide, Q is an aliphatic tertiary amine, f is 0.1–5 mmol/g bactericide.

2. The bactericide according to claim 1, wherein said resin is a polystyrene resin or a gel or is a macroporous resin obtained by copolymerizing styrene and divinylbenzene, R is $C_6$–$C_{20}$ alkyl, R' is $C_1$–$C_{12}$ alkyl, m value is 0.1–0.8 mmol/g bactericide, n is an integer of 3–8, $R_1$, $R_2$ and $R_3$ are $C_1$–$C_6$ alkyl, k value is 0.1–1 mmol/g bactericide, m value is not greater than k value in formulae II and IV, f value is 0.1–5 mmol/g bactericide, Q is a $C_1$–$C_{18}$ trialkyl tertiary amine containing one N atom or a tertiary amine containing several N atoms having the structural formula $R_a R_b N(CH_2)_p NR_c R_d$, wherein $R_a$, $R_b$, $R_c$ and $R_d$ is $C_1$–$C_{18}$ alkyl, p is an integer of 1–10.

3. The bactericide according to claim 2, wherein said gel has a crosslinked degree of 1–15%, said macroporous resin has a crosslinked degree of 1–20%, R is $C_6$–$C_{16}$ alkyl, m value is 0.1–0.4 mmol/g bactericide, n is an integer of 3–6, $R_1$, $R_2$ and $R_3$ are $C_1$–$C_4$ alkyl, k value is 0.1–0.4 mmol/g bactericide, m value is not greater than k value in formulae II and IV, f value is 0.4–3.5 mmol/g bactericide, Q is a $C_1$–$C_{12}$ trialkyl tertiary amine containing one N atom or a tertiary amine containing several N atoms having the structural formula: $R_a R_b N(CH_2)_p NR_c R_d$, wherein $R_a$, $R_b$, $R_c$, and $R_d$ is $C_1$–$C_{12}$ alkyl: p is an integer of 1–8.

4. The bactericide according to claim 3, wherein said gel has a crosslinked degree of 1–4%, and said macroporous resin has a crosslinked degree of 1–10%, Q is a trialkyl tertiary amine containing one N atom and at least one C1–C6 alkyl, or a tertiary amine containing several N atoms having the structural formula: $R_a R_b N(CH_2)_p NR_c R_d$, wherein at least one alkyl in $R_a$, $R_b$, $R_c$, and $R_d$ is $C_1$–$C_6$ alkyl: p is an integer of 2–5.

5. The bactericide according to claim 1, wherein $X^{-a}$ is selected from $Cl^-$, $Br^-$, $I^-$, $NO_3^-$, $SO_4^{2-}$, $CO_3^{2-}$ and $OH^-$; and a is 1 or 2.

* * * * *